(12) United States Patent
El-Deiry et al.

(10) Patent No.: US 7,553,955 B2
(45) Date of Patent: Jun. 30, 2009

(54) MOLECULAR BEACONS, METHODS AND KITS FOR DETECTING DNA DAMAGE RESPONSE

(75) Inventors: Wafik S. El-Deiry, Philadelphia, PA (US); Rishita Shah, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/514,316

(22) Filed: Sep. 1, 2006

(65) Prior Publication Data
US 2007/0178485 A1     Aug. 2, 2007

Related U.S. Application Data

(60) Provisional application No. 60/712,821, filed on Sep. 1, 2005.

(51) Int. Cl.
*C07H 21/04*    (2006.01)
*C12P 19/34*    (2006.01)

(52) U.S. Cl. ..................................... 536/24.3; 435/91.2

(58) Field of Classification Search ....................... None
See application file for complete search history.

(56) References Cited

U.S. PATENT DOCUMENTS 6,083,695 A * 7/2000 Hardin et al. .................. 506/5

OTHER PUBLICATIONS

Tsourkas et al. Nucleic acids Research, vol. 30, No. 23, pp. 5168-5174, 2002.*
Kreeger, Karen., University of Pennsylvania, Abramson Cancer Center News, pp. 1-4, Nov. 30, 2004 (http://www.penncancer.com/penn_news.cfm).*

* cited by examiner

*Primary Examiner*—Gary Benzion
*Assistant Examiner*—Cynthia B Wilder
(74) *Attorney, Agent, or Firm*—Mark S. Cohen; Pearl Cohen Zedek Latzer, LLP

(57) ABSTRACT

This invention relates to embodiment to a molecular beacon, methods and kits for the detection of expression of p21(Waf1/Cip1), in response to chemotherapy. Specifically, the introduction of a phosphorothioate-modified p21-beacon by transfection in human tumor cells yields increased signal in a dose dependent manner.

23 Claims, 5 Drawing Sheets

MOLECULAR BEACONS, METHODS AND KITS FOR DETECTING DNA DAMAGE RESPONSE

CROSS REFERENCE TO RELATED APPLICATIONS

This application claims priority from U.S. Provisional Application Ser. No. 60/712,821, filed Sep. 1, 2005, which is incorporated herein by reference in its entirety

GOVERNMENT INTEREST

A portion of this work was funded by the National Institutes of Health under grant numbers U54 CA105008. The government may own certain rights in the present invention.

FIELD OF INVENTION

This invention is directed to a molecular beacon, methods and kits for the detection of expression of p21(WAF1/CIP1), in response to chemotherapy. Specifically, the introduction of a phosphorothioate-modified p21-beacon by transfection in human tumor cells yields increased signal in a dose dependent manner.

BACKGROUND OF THE INVENTION

Molecular beacons were introduced in the mid-1990's as novel probes that can fluorescently detect in solution or in living cells nucleic acid synthesis, expression or trafficking. The basic structure of molecular beacons includes a stem-loop structure with a fluorophore and a quencher at the respective 5' and 3' ends of the molecule. Proximity of the fluorophore to the quencher results in fluorescence resonance energy transfer and quenching of the fluorescence. Upon hybridization of the loop region to a target DNA or RNA in solution or in living cells, the fluorophore and quencher become spatially separated resulting in emission of fluorescence. Molecular beacons have been widely used to detect either DNA or RNA in the real-time quantitative PCR methodologies. Microinjection of antisense oligonucleotide molecular beacons designed to detect the myb/vav protooncogene in human K562 leukemia cells provided evidence for DNA-RNA hybridization in living cells.

One of the potential targets for real-time in vivo imaging with molecular beacons is the p53 pathway which, since dysfunctional in cancer, portends a poor patient prognosis and poor response to chemo- and radiotherapy. Mutations in the p53 gene are common in human tumors and even when the gene is wild-type there are usually other defects resulting in p53 inactivity. Mechanisms of p53 inactivation include accelerated degradation due to MDM2 or human papillomavirus E6 protein, cytoplasmic sequestration due to Parc, inefficient stabilization due to ARF deletion or mutation, or dominant negative isoforms of p53 family members. While detection of p53 mutation in vivo may be potentially useful in prognostication, this has proven to be difficult for a variety of reasons.

p53 mutations occur at many different sites primarily within a large central DNA-binding domain, and while it is possible to detect such mutations with microarray technology this requires DNA isolation. Immunohistochemistry has been used to detect overexpressed p53 protein due to the fact that most mutants have a greatly increased half-life. However, increased expression of p53 occurs even when p53 is wild-type and so this has not been a uniformly reliable method. While there are some antibodies that can distinguish wild-type from some mutated epitopes of p53, these methods require at a minimum fixing the cells and therefore cannot be used in living tissue.

In the last decade, significant progress has been made in the identification and characterization of the events downstream of p53 activation. Wild-type p53 protein is stabilized in response to a variety of cellular stresses including exposure to DNA damaging chemo- or radio-therapy, hypoxia, or inappropriate proliferative signals such as oncogene activation. Transcriptional targets of p53 have been linked to its tumor suppressive activities. For example, the p53-dependent transcriptional activation of p21(WAF1/CIP1) in response to cellular stress results in cell cycle arrest through inhibition of cyclin-dependent kinase activity.[5,6] Other p53 targets include death receptors such as Fas or KILLER/DR5, or other proapoptotic genes such as Puma, Noxa, Bax, Bak, Bid, or PIDD that either directly or indirectly impact on the mitochondria or caspase activation leading to cell death. The most consistently induced p53 target gene is the p21(WAF1/CIP1) gene, being induced during either cell cycle arrest or apoptosis or in all tissues or cell lines examined.

Therefore, there is a need to non-invasively imaging cellular and molecular events associated with effective chemotherapy and radiotherapy that use p21(WAF1/CIP1) gene.

SUMMARY OF THE INVENTION

In one embodiment, the invention provides a molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2).

In another embodiment, the invention provides a method of evaluating the efficiency of a cancer chemotherapy in a subject comprising: contacting a cancerous cell of said subject with an effective concentration of a molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2); and comparing a detected signal to a control.

In one embodiment, the invention provides a kit for performing an evaluation of the efficiency of chemotherapy of a cancer in a subject, the kit comprising a molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2).

DETAILED DESCRIPTION OF THE INVENTION

Figure 1:
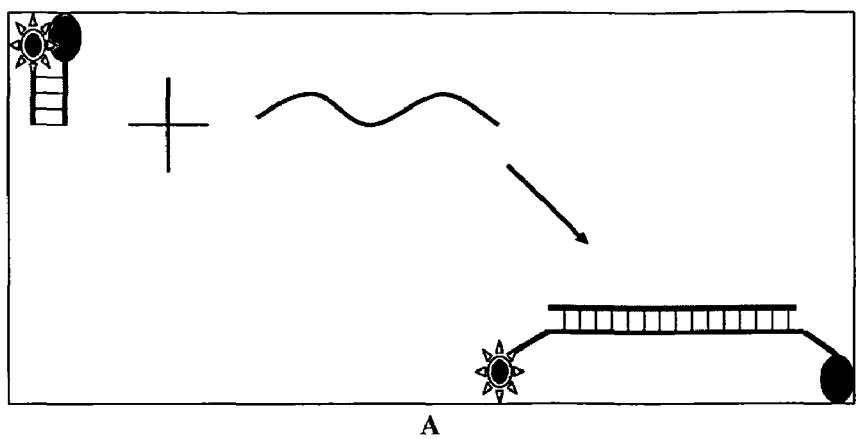
FIG. 1 shows synthesis and Design of p21 beacon. A) Schematic representation of a molecular beacon. When the beacon hybridizes to the target mRNA sequence, the fluorophore is removed from the vicinity of the quencher, and a signal is emitted. B) Examples of secondary structures of p21 mRNA obtained from web server. C) Sequence and probable secondary structure of designed beacon. The fluorophore is linked to the 5' end, and a quencher is linked to the 3' end.
Figure 1:
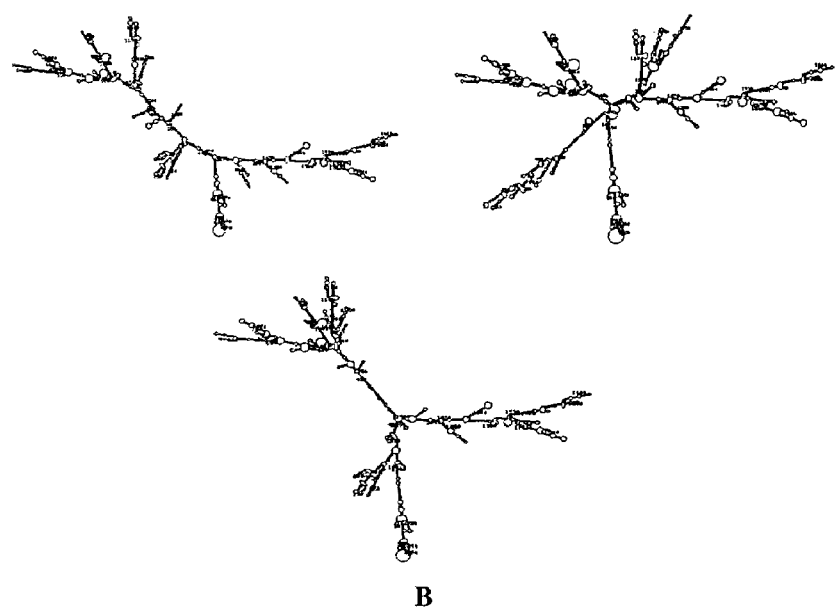
Figure 1:
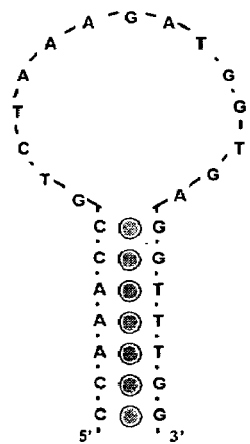

This invention relates in one embodiment to a molecular beacon, methods and kits for the detection of expression of p21(WAF1/CIP1), in response to chemotherapy. Specifically, the introduction of a phosphorothioate-modified p21-beacon by transfection in human tumor cells yields increased signal in a dose dependent manner.

Molecular Beacons comprise in one embodiment, nucleic acid molecules having a target complementary sequence, an affinity pair (or nucleic acid arms) holding the probe in a closed conformation in the absence of a target nucleic acid sequence, and a label pair that interacts when the probe is in a closed conformation. In another embodiment, hybridization of the target nucleic acid and the target complementary sequence separates the members of the affinity pair, thereby shifting the probe to an open conformation. The shift to the open conformation is detectable in one embodiment due to reduced interaction of the label pair, which may be, in one embodiment, a fluorophore and a quencher (e.g., DABCYL and EDANS). Molecular Beacons are fully described in U.S. Pat. No. 5,925,517, the disclosure of which is hereby incorporated by reference.

According to this aspect of the invention and in one embodiment, the invention provides molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2).

In one embodiment, the molecular beacon of the invention comprises a detectable label in the 5' or 3' ends of the stem. The term "detectable label" refers in one embodiment to a composition or moiety that is detectable by spectroscopic, photochemical, biochemical, immunochemical, electromagnetic, radiochemical (using technetium-99m ($^{99m}$Tc) e.g.), or chemical means such as fluorescence, chemifluoresence, or chemiluminescence, or any other appropriate means. In another embodiment, detectable labels are fluorescent dye molecules, or fluorophores, such fluorescein, phycoerythrin, CY3, CY5, allophycocyanine, Texas Red, peridenin chlorophyll, cyanine, FAM, JOE, TAMRA, TET, VIC. Methods and compositions for detectably labeling molecules, such as oligonucleotides, PNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

In one embodiment, the photoluminescent dye used in the beacons, methods and kits of the invention is fluorescein, phycoerythrin, CY3, CY5, allophycocyanine, Texas Red, peridenin chlorophyll, cyanine, FAM, JOE, TAMRA, TET, VIC, or a combination thereof. In another embodiment, the FAM is 6-carboxyfluorescein (6-FAM).

In one embodiment, molecular beacon probes according to the present invention utilize any photoluminescent moiety as a detectable moiety. Typically these are dyes. In another embodiment these are fluorescent dyes. Photoluminescence is any process in which a material is excited by radiation such as light in one embodiment, is raised to an excited electronic or vibronic state, and subsequently re-emits that excitation energy as a photon of light. Such processes include in one embodiment fluorescence, which denotes emission accompanying descent from an excited state with paired electrons (a "singlet" state) or unpaired electrons (a "triplet" state) to a lower state with the same multiplicity, i.e., a quantum-mechanically "allowed" transition. Photoluminescence includes in another embodiment phosphorescence which denotes emission accompanying descent from an excited triplet or singlet state to a lower state of different multiplicity, i.e., a quantum mechanically "forbidden" transition. Compared to "allowed" transitions, "forbidden" transitions are associated with relatively longer excited state lifetimes In one embodiment, the molecular beacon of the invention, which is used in the methods and kits of the invention, comprises a quencher moiety of a detectable label disposed on the opposing end of the detectable label. In another embodiment, "quencher moiety" as used herein means a molecule that, in close proximity to a donor fluorophore, takes up emission energy generated by the donor and either dissipates the energy as heat or emits light of a longer wavelength than the emission wavelength of the donor. In one embodiment, the quencher is considered to be an acceptor fluorophore. The quenching moiety can act in another embodiment, via proximal (i.e. collisional) quenching or by Forster or fluorescence resonance energy transfer ("FRET") in other embodiments. Quenching by FRET is used in one embodiment when TAQMAN™ probes are used while in another embodiment, proximal quenching is used in molecular beacon and scorpion type probes.

In one embodiment, the molecular beacon used in the invention utilize proximal quenching. In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on $R^{-6}$, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore). TaqMan™ probes (Heid et al., 1996) use the fluorogenic 5' exonuclease activity of Taq polymerase to measure the amount of target sequences in cDNA samples. TaqMan™ probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi et al., Nature Biotechnology 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

In one embodiment, the kits and methods of the invention use binary molecular beacons. In another embodiment, since molecular beacons generate a detectable background fluorescence it is beneficial to validate that fluorescence signals are the result of hybridization of the molecular beacon to the target sequence rather than merely the presence of the probe in the sample. In on embodiment, two different molecular beacons with the same loop specificity, each possessing a differently colored fluorophore, are designed to bind to the same target at nearly adjacent positions so that, on hybridization, their fluorophores interact via FRET as described herein. In another embodiment, since the efficiency of FRET is inversely proportional to the distance between the fluorophores, molecular beacons that are bound nonspecifically to the target sequence, fluoresce in their own characteristic emission wavelength but do not to participate in the generation of a FRET signal. In one embodiment, the donor fluorophore (TMR e.g.) is placed at the 5' end of one molecular beacon of the invention and the acceptor fluorophore (Texas red) at the 3' end of the other molecular beacon of the invention, to maximize the efficiency of target-mediated FRET. The fluorophore-bearing arms, or stems of these molecular beacons (as well as the loop sequences) were designed to be complementary to their target sequences. In one embodiment, the sequences of the two probes are chosen so that, when they both bind to the same target sequence, their fluorophores are separated from each other by such number of intervening target nucleotides, so that the intensity of the FRET signal is at a maximum, optimally balancing the negative effect of mutual fluorescence quenching and the positive effect of resonance energy transfer for these particular fluorophores. In one embodiment, the kits of the invention comprise binary molecular beacon system.

Suitable donor fluorophores for use in the molecular beacons, kits and methods of the invention include 6-carboxyfluorescein (6FAM), tetrachloro-6-carboxyfluorescein (TET), 2'-chloro-7'-phenyl-1,4-dichloro-6-carboxyfluorescein (VIC), and the like. Suitable quenchers include tetramethylcarboxyrhodamine (TAMRA) 4-(4-dimethylaminophenylazo)benzoic acid ("DABCYL" or a DABCYL analog) and the like. Tetramethylrhodamine (TMR) or 5-carboxyrhodamine 6G (RHD) may be combined as donor fluorophores with DABCYL as quencher. Probes for detecting amplified sequence in real time may be stored frozen (−10. to −30° C.) as 100 M stocks. TaqMan MGB probes are available from Applied BioSystems (4316032).

Examples of donor/acceptor label pairs that may be used in connection with the invention, include in one embodiment fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, 6-FAM/BHQ1 and fluorescein/QSY7 dye. A person holding an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL in one embodiment, and the QSY 7 dyes in other embodiments, advantageously eliminate the potential problem of background fluorescence resulting from direct (i.e., non-sensitized) acceptor excitation. In one embodiment, fluorophore moieties that can be used as one member of a donor-acceptor pair include fluorescein, ROX, and the CY dyes (such as CY5). In another embodiment, quencher moieties that can be used as another member of a donor-acceptor pair include DABCYL and the BLACK HOLE QUENCHER moieties which are available from Biosearch Technologies, Inc., (Novato, Calif.).

In one embodiment, the kits and methods of the invention use molecular beacons labeled with colloidal quantum dots. Colloidal quantum dots (QDs) refer in one embodiment to semiconductor nanocrystals whose photoluminescence emission wavelength is proportional to the size of the crystal. The emission spectra of QDs are narrow, which allows multiwavelength labeling with different sizes of QDs with little overlap. QDs outer surfaces is readily conjugated in another embodiment to the molecular beacons of the invention, resulting in a spectrum of labels that are all excited with a single wavelength. In another embodiment, the QDs used in the invention are CdSe nanocrystals.

In one embodiment, in addition to p21-specific molecular beacons, the methods and kits of the invention comprise molecular beacons specific for other cancer-related genes, such as Puma, or KILLER/DR5, Bax, Bid, FADD, FLIP, IAP1, IAP2, Bcl-XL, Plk2, Caspase 6, Cyclin D, Fas ligand, TRAIL, Caspase 8, Apaf1, p27 in other embodiment.

In one embodiment QDs of different size are used to label the molecular beacons specific for the above mentioned genes or protein encoding genes, such that an emmission fingerprint emerges, which will identify the presence of any combination of the genes present in the sample. In one embodiment, the obtained sample fingerprint is compared with a standard fingerprint of a sample taken from a subject with a given cancer type. In another embodiment, emmission spectra library of cancer specific molecular beacons of the invention labeled with the QDs is used to determine the molecular beacon cocktail necessary to diagnose a given cancer type. In one embodiment, the kits of the invention comprise cancer specific cocktail of molecular beacons.

In one embodiment, the invention provides a molecular beacon oligonucleotide comprising a stem and a loop structure, wherein said loop has a sequence complementary to a coding, or non coding region of p21 (WAF1/CIP1) gene. In another embodiment, "complementary" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of p21 (WAF1/CIP1) gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches.

In one embodiment, the invention provides a molecular beacon oligonucleotide comprising a stem and a loop structure, wherein said loop has a sequence complementary to a coding region of p21 (WAF1/CIP1) gene. The term "coding region" refers in one embodiment to a sequence of a nucleic acid or its complement, or a part thereof, that can be transcribed and/or translated to produce the mRNA for and/or the polypeptide or a fragment thereof. IN another embodiment, coding sequences include exons in a genomic DNA or immature primary RNA transcripts, which are joined together in one embodiment, by the cell's biochemical processes, providing a mature mRNA. The anti-sense strand is the complement of such a nucleic acid, and the skilled artisan would readily recognize that the encoding sequence can be deduced therefrom.

In another embodiment, the invention provides a molecular beacon oligonucleotide comprising a stem and a loop structure, wherein said loop has a sequence complementary to a non-coding region of p21 (WAF1/CIP1) gene. In one embodiment, the term "non-coding region" refers to a sequence of a nucleic acid or its complement, or a part thereof, that is not transcribed into amino acid in vivo, or where tRNA does not interact to place or attempt to place an amino acid in another embodiment. Non-coding sequences include in one embodiment both intron sequences in genomic DNA or immature primary RNA transcripts, and gene-associated sequences such as promoters, enhancers, silencers, etc., in other embodiments.

In one embodiment, the invention provides a molecular beacon comprising: an oligonucleotide comprising a stem and a loop structure, wherein the structure comprises a nuclease resistant backbone.

In one embodiment, the sensitivity of cellular imaging and quantification of gene expression using molecular beacons is severely limited by the degradation of oligonucleotide backbone by nucleases. To overcome this difficulty, molecular beacons are synthesized in another embodiment with nuclease-resistant backbone chemistries, such as phosphorothioate in one embodiment, or peptide nucleic acid (PNA) and 2'-O-methyl modifications in other embodiments. According to this aspect of the invention and in one embodiment, the nuclease resistant chemistry used in the beacons, methods and kits of the invention comprises phosphorothioate-modified backbone.

In one embodiment, beacons modified with sugar modified-'North' (3'-endo-2'-exo) conformationally constrained nucleosides, or base-constraining oxetane (OXE) modifications (oxetane, 1-(1',3'-O-anhydro-β-D-psicofuranosyl nucleosides), are used to protect the beacon from nuclease activity by modifying the beacon's backbone. The modifications, in another embodiment makes the beacon so modified be delivered to the cells with greater efficiency, making resolution of the methods and kits of the invention higher and detection more accurate.

In another embodiment, the invention provides a molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases, and wherein said loop has a sequence complementary to a coding, or non coding region of p21 (WAF1/CIP1) gene.

In one embodiment, the p53 gene is inactivated in the majority of human cancers, affecting cell division and apoptosis processes. In another embodiment, DNA-damaging agents induce a p53-dependent G1 arrest that is critical for p53-mediated tumor suppression. In one embodiment, following DNA damage, cells can either proceed to apoptosis or enter a transient arrest cycle, allowing time for DNA repair. p21 gene, also known as WAF1 or CIP1, is a key component of this pathway. In one embodiment, it is up-regulated by activated wild type p53, which acts as a transcription factor. p21 expression results in inhibition of the cyclin-dependent kinases (Cdks), that are essential for cell division. Consequently, cell cycle is arrested at the G1 phase, until genomic repair is established.

p53 is tightly regulated, and its protein level in normal cells is very low. The p53 protein is regulated largely at the post-translational level through its interaction with MDM2. MDM2 restricts p53 transactivation function by binding to the N-terminal domain of p53, mediating ubiquitination and rapid degradation of p53 by proteasomes. In cancer cells, mutant p53 loses its transactivation function in one embodiment, and does not induce MDM2 gene expression. In another embodiment mutant p53 is not degraded in cancer cells and its half-life is prolonged. In one embodiment, effective chemotherapy will increase activity of p53, thereby inducing p21 activity. In another embodiment, increase in p21 activity is accompanied by cellular concentration of p21 mRNA, which is detectable by the beacons, methods and kits of the invention.

In one embodiment, the beacons used in the invention are sufficiently complimentary to the p21 gene to be detected. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, 2.sup.nd ed. (Cold Spring Harbor Laboratory Press, Cold Spring Harbor, N.Y., 1989).

In another embodiment, the invention provides a molecular beacon comprising an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2), wherein the loop has a sequence complementary to the third exon of the p21 (WAF1/CIP1) gene. In another embodiment, that sequence comprises 5'-GTC TAA AGA TGG TGA-3' (SEQ ID NO.3).

In one embodiment, the tendency of molecular beacons to shuttle into the nucleus soon after they entered the cell directed the identification of the intron/exon boundaries in the mRNA and direct the target sequence to be contained only in the third exon.

In one embodiment, the invention provides a method of evaluating the efficiency of cancer chemotherapy in a subject comprising: contacting a tumor cells of said subject with an effective concentration of the molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCG-GTTTGG-3' (SEQ ID NO.2); and comparing detected signal to a control.

In one embodiment, the methods of the invention use the molecular beacons described in the embodiments herein. In another embodiment, the controls used for comparing the results are the same standards used in the kits of the invention, described herein.

In another embodiment the methods and kits of the invention are used to evaluate the efficacy of therapy of a cancer. In one embodiment, the cancer is lung cancer, or colon cancer, breast cancer, prostate cancer, squamous cell carcinoma, bone cancer or prostate cancer, or combination thereof in other embodiments.

In one embodiment, the effective concentration of the molecular beacon used in the methods and kits of the invention is between about 5 and 400 nM. In another embodiment, the effective concentration of the molecular beacon is between about 5 and 50 nM, or in another embodiment between about 50 and 100 nM, or in another embodiment between about 100 and 150 nM, or in another embodiment between about 150 and 200 nM, or in another embodiment between about 200 and 250 nM, or in another embodiment between about 250 and 300 nM, or in another embodiment between about 300 and 350 nM, or in another embodiment between about 350 and 400 nM. In one embodiment, the effective concentration of the molecular beacon used in the methods of the invention is 200 nM.

A person skilled in the art would recognize that the effective concentration of the molecular beacons used in the methods and kits of the invention could be altered to yield an optimal signal-to-noise response, based on the source of cancerous cell and the particular purpose for which it is being used, all without departing from the scope of the invention. In one embodiment, the effective concentration of the molecular beacon used in the methods and kits of the invention would be a function of the label/quencher combination used, or in another embodiment, the cancer type sought to be evaluated, or in another embodiment, the chemotherapy agent used.

In one embodiment, the invention provides a method of evaluating the efficacy of chemotherapy for cancer in a subject, comprising contacting a cancerous cell, or a cell suspected of being malignant in another embodiment, with the beacons of the invention or using the kits of the invention, wherein contacting the cell further comprises amplification of the target sequence of said molecular beacon. In one embodiment, the amplified target sequence is complementary to the sequence of p21 (WAF1/CIP1), which in another embodiment will comprise 5'-GTC TAA AGA TGG TGA-3' (SEQ ID NO.3).

In one embodiment, the term "amplification" or "amplify" refers to one or more methods known in the art for copying a target nucleic acid, thereby increasing the number of copies of a selected nucleic acid sequence. Amplification may be exponential in one embodiment, or linear in another. In one embodiment, a target nucleic acid may be either DNA or RNA. The sequences amplified in this manner form an "amplicon." While the exemplary embodiments described herein relate to amplification using the polymerase chain reaction ("PCR"), numerous other methods are known in the art for amplification of nucleic acids (e.g., isothermal methods, rolling circle methods, etc.) and are considered within the scope of the present invention. The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860.

In another embodiment, real time PCR is used in the methods of the invention. The term "real time PCR" refers in one embodiment to the process where a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is based in one embodiment on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehe et al., J. Virol. Meth. 102:37-51 (2002); and Aldea et al., J. Clin. Microbiol. 40:1060-1062 (2002) (referring to the "LightCycler," where real-time, kinetic quantification allows measurements to be made during the log-linear phase of a PCR).

In one embodiment, real time PCR or other detection methods are used to detect activation of p53 gene in the sample collected from the subject. In another embodiment, molecular beacons, specific for the p53 gene are used as part of the methods and kits of the invention, wherein samples are split and the detectable signal from the bound molecular beacon, or labeled p53-specific antibody, which could either be monoclonal or polyclonal antibody or a fragment thereof (F(ab') e.g.), is compared with a sample following digestion with an endonuclease. In one embodiment, the more efficient the chemotherapy, the higher will be the p53 activation.

In one embodiment, the cells used for the methods of the invention are obtained from a sample given by the subject. The sample to be analyzed may consist in one embodiment of, or comprise blood, sera, urine, feces, epidermal sample, skin sample, cheek swab, sperm, amniotic fluid, cultured cells, bone marrow sample and/or chorionic villi, and the like. A biological sample may be processed in another embodiment to release or otherwise make available a nucleic acid for detection as described herein. Such processing may include in one embodiment steps of nucleic acid manipulation, e.g., preparing a cDNA by reverse transcription of RNA from the biological sample. Thus, the nucleic acid to be amplified in one embodiment by the methods of the invention may be DNA or RNA.

The term "about" as used herein means in quantitative terms plus or minus 5%, or in another embodiment plus or minus 10%, or in another embodiment plus or minus 15%, or in another embodiment plus or minus 20%.

In one embodiment, the invention provides a kit for performing an evaluation of the efficiency of chemotherapy of a cancer in a subject, the kit comprising a molecular beacon comprising: an oligonucleotide comprising a stem and a loop structure and having a photoluminescent dye at one of the 5' or 3' ends and a quenching agent at the opposite 3' or 5' ends, wherein said loop consists of about 12-25 bases and has a melting temperature ($T_m$) of 52-54° C., and wherein the stem consists of 7 base pairs having a sequence comprising 5'-CCAAACCGGTTTGG-3' (SEQ ID NO.2).

In another embodiment, the cancer type in which the chemotherapy efficiency is sought to be evaluated is a cancer exhibiting depletion, or in another embodiment, down-regulation of the expression of the p53 gene, or its products.

In one embodiment, the kits of the invention may further comprises a positive and/or negative standard, wherein the standard can be assayed and compared to the test sample. It is to be understood that the kits of the invention may be modified and marketed for particular use, which in one embodiment are cancer-specific.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, and in another embodiment, will be suitable for a particular application of the kit.

In one embodiment, the kit of the invention may further comprise a software package contained on a computer storage medium, with a program for correlating values obtained with a standard, for storing and comparing, by date, or in another embodiment for extrapolating results obtained.

In the methods and kits according to embodiments of the present invention, data relating to values obtained for the parameters for malignant and non-malignant samples analyzed may be provided in a database such as Microsoft Access, Oracle, other SQL databases or simply in a data file. The database or data file may contain in one embodiment, a patient identifier such as a name or number, the values obtained, patient prognosis, age of onset of symptoms, therapy regimen, and other identifying and relevant characteristics, as will be understood by one skilled in the art. The database may contain, in other embodiments, the change in any of the parameters analyzed, as a function of time, or chemotherapy regimen, or a combination thereof. In one embodiment, the methods and kits of this invention may further comprise accessing a memory, or a means thereto for storing the obtained values for the parameters, and other data as described herein. In another embodiment, the methods of this invention may further comprise generating and graphically displaying the values obtained. In one embodiment, the analysis is executed by a processor or a virtual computer program.

In one embodiment the software incorporates statistical tools for determining the significance of the findings. Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0.1, 0.05, 0.025, 0.02, 0.01, 0.005, 0.001, 0.0001, or less is indicative of a significant difference.

As used herein, "subject" refers to a human or any other animal which contains a p21 gene that can be detected using the molecular beacons, methods and kits described herein. A subject can be a patient, which refers to a human presenting to a medical provider for diagnosis or treatment of a disease. A human includes pre and post natal forms. In one embodiment, subjects are humans being tested for the efficacy of chemotherapy for the treatment of cancer.

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments. "Treating" embraces in another embodiment, the amelioration of an existing condition. The skilled artisan would readily recognize that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. In one embodiment, the efficacy of chemotherapy for the treatment of cancer for the purpose described herein, is done using the methods described herein.

The following examples are presented in order to more fully illustrate the preferred embodiments of the invention. They should in no way be construed, however, as limiting the broad scope of the invention.

EXAMPLES

Materials and Methods:

p21 Beacon Design and Synthesis p21 antisense oligonucleotides, ordered from GeneLink (Hawthorne, N.Y.), contained the sequence is 5'-CCAAAC-CGTCTAAAGATGGTGAGGTTTGG-3' (SEQ ID NO.1). 6-FAM was attached to the 5' end, and BHQ1 to the 3' end. For stability, the oligonucleotide was constructed using a phosphorothiolated backbone. The antisense beacon was developed from human p21 mRNA sequence (accession number NM_000389). The beacon was resuspended in TE buffer, and stored in the dark at −20 degrees Celsius. A more detailed explanation of molecular beacon design can be found at www.molecular-beacons.org.

Cell Lines and Culture Methods

H460 is a human non-small cell lung cancer cell line that expresses wild-type p53 and p21.[9] H460 cells were grown in RPMI media containing 10% fetal bovine serum (FBS) and 1% penicillin and streptomycin (PS). HCT116 is a human colon adenocarcinoma cell line that expresses wild-type p53 and p21.[9] p21-null HCT116 cells have been previously described.[10,11] HCT116 cells were grown in McCoy's 5A media with 10% FBS and 1% PS. P53-null HCT116 and mutant p53-expressing DLD1 human colon carcinoma and p21-null DLD1 derivatives have been previously described.[12] DLD1 cells were grown in Dulbecco's Modified Eagle Media with 10% FBS and 1% PS. To induce expression of p21, cells were treated with 0.2 micrograms/mL of Adriamycin.

Transfection of p21 Beacon in Living Tumor Cells

Cells were grown to 90% confluency in six well plates and transfected using 4 microL of Lipofectamine 2000 obtained from Invitrogen Life Technologies, Inc. (Carlsbad, Calif.). Increasing concentrations of beacon was added to each well to achieve final concentrations ranging between 0 and 400 nM. Transfections were carried out in serum free media for four hours, and a period of 24 hours passed before cells were treated with Adriamycin.

Monitoring of p21 Beacon Activation in Living Cells

Living cells were detected using a Zeiss AxioVert inverted microscope (Carl Zeiss, Inc.) at 40× magnification. Green fluorescence was visualized by exciting at 470 nm with a mercury arc lamp, and emissions were detected with a 515 nm long pass filter.

Example 1 p53-Dependent Activation of a Molecular Beacon in Tumor Cells Following Exposure to Doxorubicin Chemotherapy A series of tests were carried out to develop a chemotherapy-inducible molecular beacon. This represents the first attempt whose intent was to understand the technology in order to improve it for in vivo use. In the present studies a beacon was generated, which detects p21 gene activation in living tumor cells, exposed to the chemotherapeutic agent doxorubicin. The results indicate that liberation of fluorescence from a phosphorothioate-modified p21 molecular beacon occurs in chemotherapy-treated cells. Insights are provided regarding the design, specificity, background and p53-dependence of chemotherapy-induced p21-beacon activation. The present studies help in improving design for accelerating the rate at which beacon cocktails are derived to begin providing prognostic information in the clinic.

Results

Synthesis and Design of a p21-Beacon

In designing a molecular beacon, two factors were considered. First, the target sequence on the mRNA of interest had to be designed such that it would be easily accessible by the probe, and second, the beacon needed to be stable within the cell. Secondary structure of the human p21 mRNA was visualized using the MFOLD server and this resulted in several unrelated possible structures (FIG. 1B). Using a p21 target sequence used in antisense studies, a region of hybridization was identified. In light of this, the intron/exon boundaries in the mRNA were identified and target sequence to be contained were designed only in the third exon. Anticipating that the beacon would be encountering mostly unprocessed RNA in the nucleus, a target sequence involving two adjacent exon sequences was avoided.

After a potential target sequence was identified, the beacon was designed. Starting with a random sequence of nucleotides for the stem structure, the probe was analyzed using the MFOLD server for both secondary structure and melting temperature. Melting temperature was determined by altering the GC content of the stem structure, as well as adjusting the overall length of the hybridization sequence. Because the half-life of most beacons upon entrance into mammalian cells is less than 15 minutes, a phosphorothioate backbone was incorporated into the design. This backbone increases the half-life of beacons to a period of 2 days. The final p21-beacon design included the hybridization sequence in the loop structure and had a melting temperature of 53.3 degrees Celsius (FIG. 1C).

Figure 2:
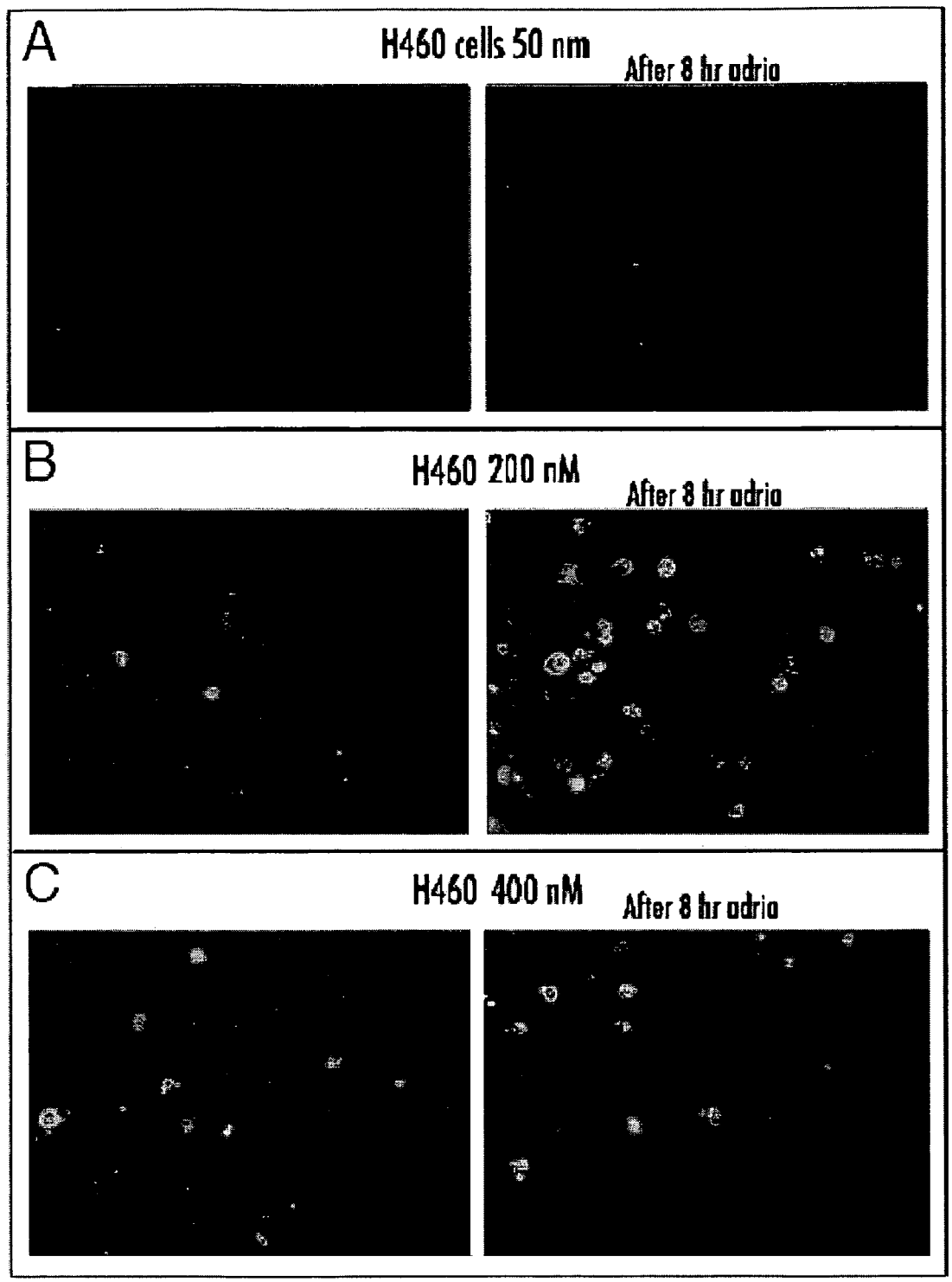
FIG. 2 shows p21 beacon dose dependent response in wild type H460 cells. Cells photographed at 40× magnification before and after treatment with adriamycin with varying concentrations of beacon. A) 50 nM B) 200 nM C) 400 nM. Photos to the left are pre-drug treatment; photos on right are after 8 hours with adriamycin.

Dose Dependence of p21-Beacon Activation in Wild-Type p53-Expressing Human H460 Lung Cancer Cells The synthetic human p21-beacon was transfected at different concentrations into confluent six-well plates containing H460 human lung cancer cells. After 24 hours, the cells were treated with doxorubicin (Adriamycin) and examined for a change in fluorescent signal. At a 50 nM concentration of p21-beacon, there was a low signal both before and after treatment, but there was a detectable increase in fluorescence after doxorubicin exposure (FIG. 2A). As can be seen in FIG. 2B, a final concentration of 200 nM of p21-beacon provided the best intensification of signal after doxorubicin exposure as compared to untreated cells. After 8 hours of drug treatment, a significant change in fluorescent signal was observed, due to the induction of p21 by doxorubicin. When the p21-beacon concentration was increased to 400 nM, it was difficult to distinguish between untreated and treated cells (FIG. 2C). The concentration of beacon was too high, which resulted in an increase in the non-specific background signal. Cells were also visualized under the same conditions without the addition of beacon, a final concentration of 0 nM, and there was no signal both in the presence or absence of adriamycin treatment. These results indicate that a drug-induced response is detected with a p21-beacon in a (beacon)-dose dependent manner. The concentration of p21-beacon required for optimal detection of signal following doxorubicin exposure was 200 nM. This was apparently enough in H460 cells to provide a large signal upon p21 induction, without high background fluorescence.

p21-Beacon Activation in Chemotherapy-Exposed Wild-Type p53-Expressing HCT116 Colon Cancer Cells that are Either Wild-Type or Null for p21

Figure 3:
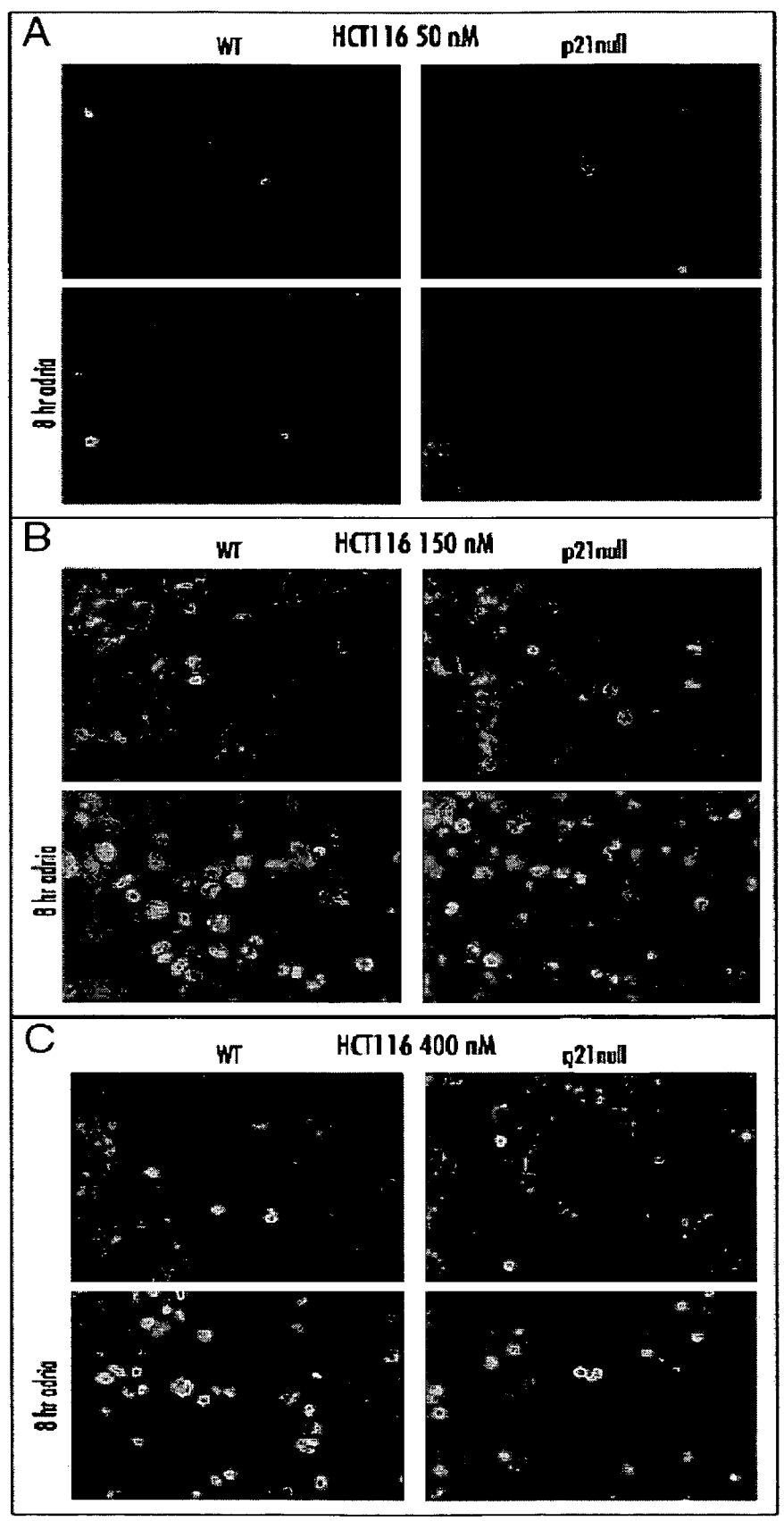
FIG. 3 shows p21-beacon activation in HCT116 cells that are either wild-type or null for p21 A) 50 nM concentration of beacon. The left column shows wild-type cells. The right column has p21 null cells. The bottom row was taken after 8 hours of adriamycin treatment. B) 150 nM of beacon. The left column shows wild-type cells. The right column has p21 null cells. The bottom row was taken after 8 hours of adriamycin treatment. C) 400 nM beacon concentration. The left column shows wild-type cells. The right column has p21 null cells. The bottom row was taken after 8 hours of adriamycin treatment.

The specificity of the p21-beacon on p21 gene sequence was examined using HCT116 human colon cancer cells that express wild-type p53 and p21, as well as p21-null HCT116 cells. Both cell types were transfected with different concentrations of p21-beacon. At 50 nM, the background signal between both wild-type and p21-null cells were similar. After drug treatment, fluorescence was induced in both cell types, and an increase in signal was seen even in the p21-null cell line (FIG. 3A). At a higher concentration of 150 nM, beacon signal was observed in both wild-type and p21-null cells, although there appeared to be a somewhat higher induction in the wild-type p21-expressing cells (FIG. 3B). The bright background was evident in the cytoplasm and appeared to move into the nucleus after doxorubicin treatment, suggesting that the drug somehow facilitated a shuttling of the oligonucleotide through the nuclear membrane. This same observation was evident in cells with a 400 nM final concentration of beacon; the signal was transferred from the cytoplasm to the nucleus after drug treatment (FIG. 3C). More overall background was present at this higher concentration, but the increase in signal was maintained in both wild-type and p21-null cells. There results indicated that there was activation of p21-beacon following chemotherapy exposure that was independent of p21 gene sequence. Endonuclease activation may contribute to the observed induction in fluorescence.

p21-Beacon Activation in Chemotherapy-Exposed p53-Null HCT116 Colon Cancer Cells or Mutant p53-Expressing DLD1 Colon Cancer Cells that are Either Wild-Type or Null for p21

Figure 4:
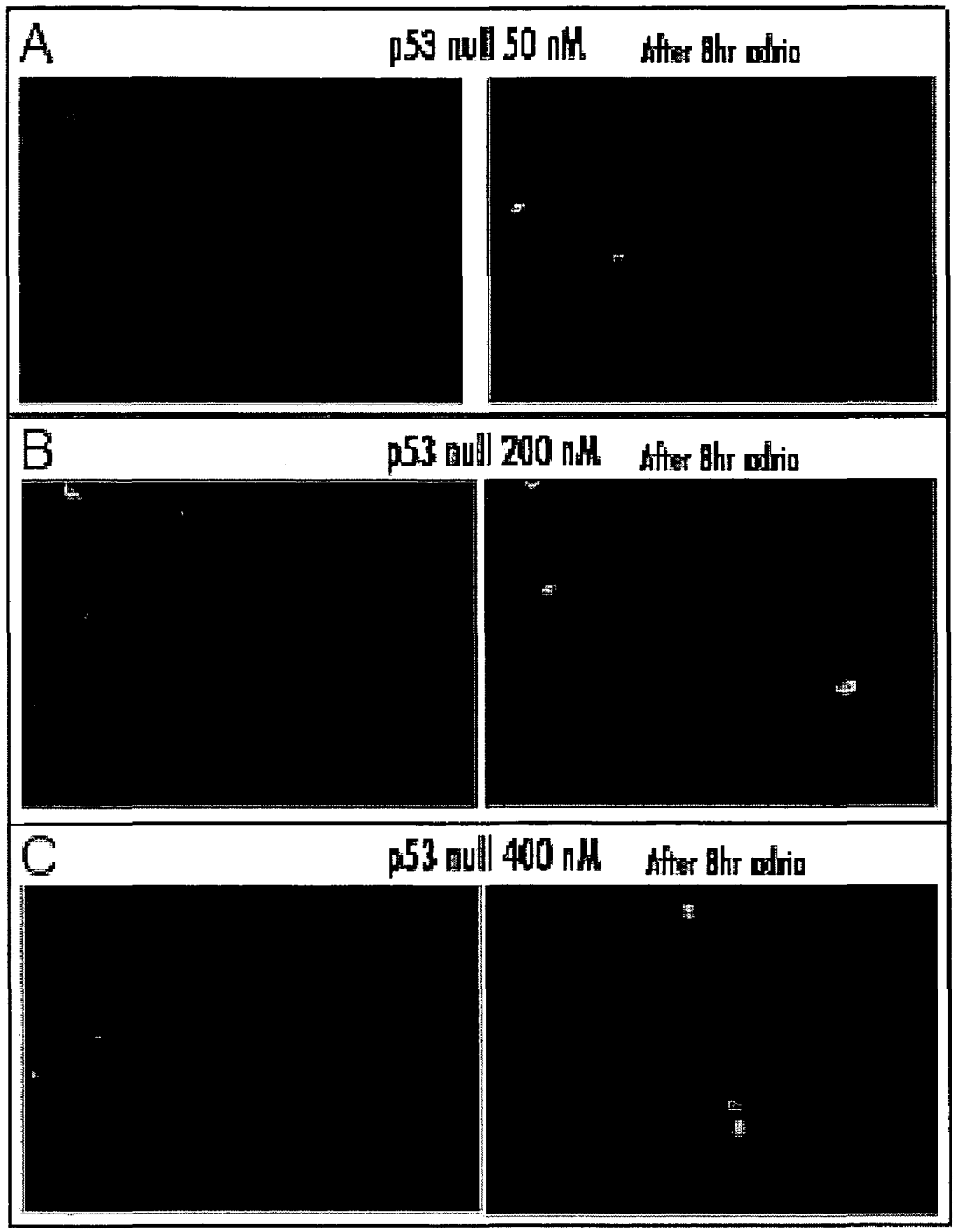
FIG. 4 shows p21-beacon activation in p53-null HCT116 or mutant p53-expressing DLD1 cells that are either wild-type or null for p21 A) HCT116 p53 null cells with 200 nM beacon. B) HCT116 p53 null cells with 400 nM beacon. C) DLD1 p21 wild-type and p21 null cells with 150 nM of beacon. p21 null cells are in column two. Drug treated cells are in the bottom row. D) DLD1 p21 wild-type and p21 null cells with 400 nM of beacon. p21 null cells are in column two. Drug treated cells are in the bottom row.
Figure 5:
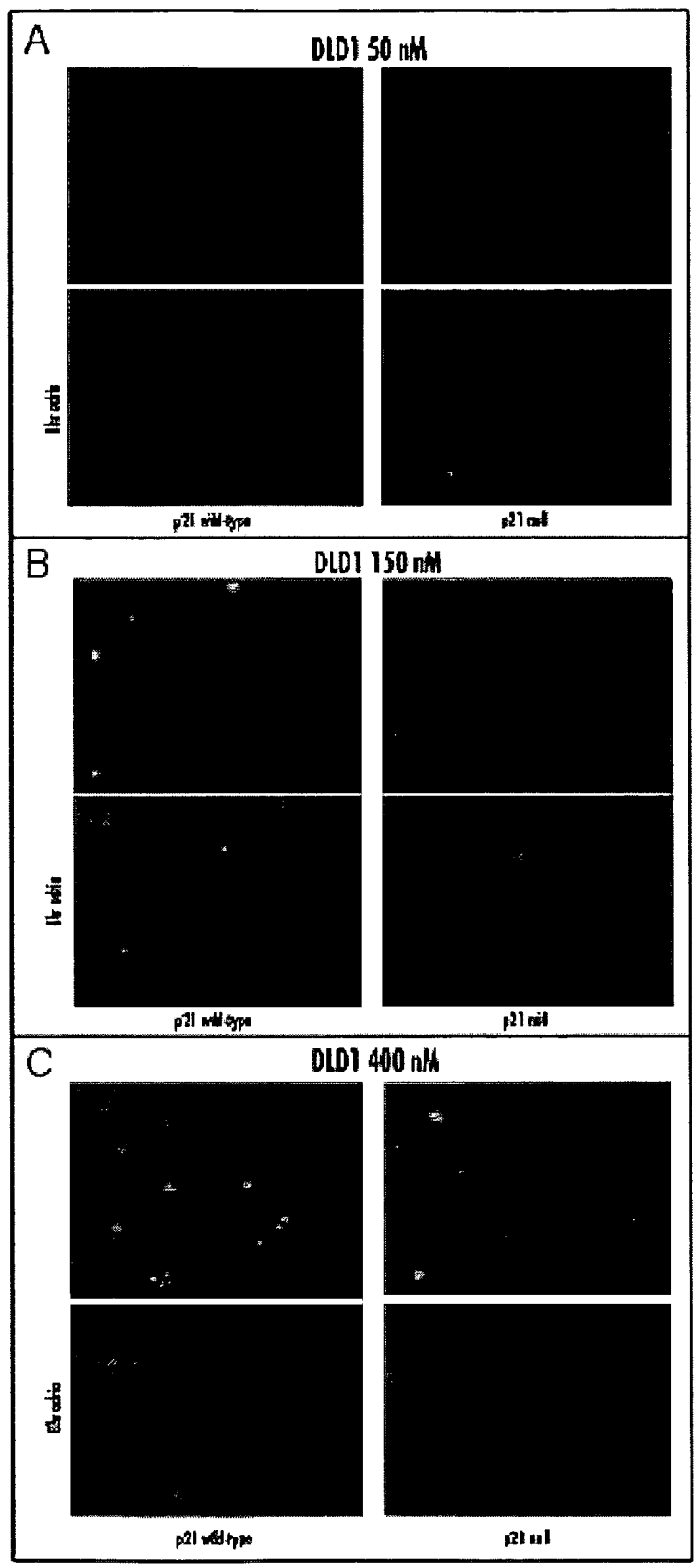
FIG. 5 shows mutant p53 expressing DLD1 cells, that are either wild-type or null for p21. A) DLD1 cells treated with 50 nM beacon. B) DLD1 cells treated with 150 nM of beacon. C) DLD1 cells treated with 400 nM of beacon. Cells in right column are p21-null. Bottom rows represent drug-treated cells.

The question of whether p21-activation following doxorubicin exposure might be affected by cells expressing wild-type p53 or were p53-deficient was examined. Transfection of p53-null HCT116 cells did not produce a concentration-dependent increase in green fluorescence. Cells treated with both 200 nM and 400 nM p21-beacon showed a similar background and minimal increase in fluorescence after doxorubicin (FIG. 4A). The p53-null cell line had little cytoplasmic background and only a few cells exhibited an intense signal after doxorubicin treatment. Mutant p53-expressing DLD1 human colon cancer cells showed a similar result between 150 nM and 400 nM concentrations of p21-beacon (FIG. 4B). Both wild-type and p21-null DLD1 cells contained a small amount of cytoplasmic background signal. Interestingly, the amount of signal in the cells appeared to decrease slightly after incubation with doxorubicin for eight hours. These results were consistent between both concentrations of p21-beacon. These results show that doxorubicin-induced activation of the human p21-beacon occurred due to a p53-dependent DNA damage response leading to both p21 gene activation and p53-dependent endonuclease activation.

Having described preferred embodiments of the invention with reference to the accompanying figures, it is to be understood that the invention is not limited to the precise embodiments, and that various changes and modifications may be affected therein by those skilled in the art without departing from the scope or spirit of the invention as defined in the appended claims.

What is claimed is:

1. A molecular beacon specific for the third exon of the p21 gene comprising: an oligonucleotide comprising a stem and a loop structure and having a photoluminescent dye at one of the 5' or 3' ends and a quenching agent at an opposite 3' or 5' ends, wherein said loop comprises the sequence set forth in SEQ ID NO: 3 and has a melting temperature ($T_m$) of 52-54° C., and wherein the stem consists of two non-contiguous stretches of base pairs having sequences comprising the sequence set forth in SEQ ID NO: 4 and the sequence set forth in SEQ ID NO: 5 and a nuclease resistant backbone.

2. The molecular beacon of claim 1, wherein said photoluminescent dye is fluorescein, phycoerythrin, cyanine dyes (CY3 and CY5) allophycocyanine, Texas Red, peridenin chlorophyll, cyanine, 6-carboxyfluorescein (6-FAM), 2',7'-dimethoxy-4',5'-dichloro-6-carboxyrhodamine (JOE), N,N,N',N'-tetramethyl-e-carboxyrhodamine (TAMRA), 2',4',1,4,- tetrachlorofluorescein (TET), and 2'-chloro-7'-phenyl-1,4-dichloro-6-carboxyfluorescein (VIC), or a combination thereof.

3. The molecular beacon of claim 1, wherein said photoluminescent dye is 6-carboxyfluorescein (6-FAM).

4. The molecular beacon of claim 1, wherein said quenching agent acts via proximal quenching or fluorescence resonance energy transfer (FRET).

5. The molecular beacon of claim 1, wherein said quenching agent is 5-2'-aminoethylamino-1-naphthalene sulfate (EDANS) or BLACK HOLE QUENCHER1 (BHQ1), a non-fluorescent quencher.

6. The molecular beacon of claim 1, wherein said nuclease resistant backbone comprises phosphorothioate, sugar modification, oxatane or combination thereof.

7. The molecular beacon of claim 1, wherein said loop has a sequence complementary to a coding, or non coding region of p21 gene.

8. A method of evaluating the efficiency of a cancer chemotherapy in a subject comprising: contacting a cancerous cell of said subject with an effective concentration of the molecular beacon of claim 1; and comparing a detected signal to a control.

9. The method of claim 8, wherein said cancer is lung cancer, colon career, breast cancer, prostate cancer, squamus cell carcinoma, bone cancer or prostate cancer.

10. The method of claim 8, wherein said effective concentration is between about 5 and about 400 nM.

11. The method of claim 10, wherein said effective concentration is between about 50 and 300 nM.

12. The method of claim 11, wherein said effective concentration is 200 nM.

13. The method of claim 8, wherein contacting further comprises amplifying the target sequence of said molecular beacon.

14. A kit for performing an evaluation of the efficiency of chemotherapy of a cancer in a subject, the kit comprising the molecular beacon of claim 1.

15. The kit of claim 14, wherein said cancer causes depletion in p53 activity.

16. The kit of claim 14, further comprising instructions for use in performing said evaluation.

17. The kit of claim 14, further comprising: a DNA polymerase; an RNA polymerase; a labeled ribonucleotide triphosphate, an unlabeled ribonucleotide triphosphate, a labeled deoxyribo-nucleotide triphosphate, an unlabeled deoxyribo-nucleotide triphosphates, labelling reagents, detection reagents, buffers or a combination thereof.

18. The kit of claim 14, further comprising one or more of: packaging materials, instructions for using the components to produce one or wore molecular beacons, one or more containers for holding the components, standards for calibrating any molecular beacon detection reaction, standard target sequences, or amplification primers for amplifying a target sequence.

19. The kit of claim 14, further comprising at least one standard, obtained from a subject, or pool of subjects, without p53 depleting cancer.

20. The kit of claim 14, further comprising at least one standard, obtained from a subject, or pool of subjects, with p53 depleting cancer.

21. The kit of claim 14, further comprising a molecular beacon specific for the sequence complementary with p53 and an endonuclease.

22. The kit of claim 21, further comprising detecting p53 activation by detecting fluorescence of a beacon, wherein the beacon is degraded by a p53-induced endonuclease.

23. The kit of claim 14, further comprising a software package, wherein said software package compares the values obtained, with the test subject to determine effectiveness of the chemotherapy.

* * * * *

UNITED STATES PATENT AND TRADEMARK OFFICE
CERTIFICATE OF CORRECTION

| | | |
|---|---|---|
| PATENT NO. | : 7,553,955 B2 | |
| APPLICATION NO. | : 11/514316 | |
| DATED | : June 30, 2009 | |
| INVENTOR(S) | : Wafik S. El-Deiry et al. | |

It is certified that error appears in the above-identified patent and that said Letters Patent is hereby corrected as shown below:

In the Specification

Please replace Column 1, Lines 13-17 with the following paragraph:

This invention was made with government support under CA105008 awarded by the National Institutes of Health. The government has certain rights in the invention.

Signed and Sealed this
Twenty-fifth Day of April, 2023

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 29
<212> TYPE: DNA
<213> ORGANISM: Human

<400> SEQUENCE: 1
ccaaaccgtc taaagatggt gaggtttgg       29

<210> SEQ ID NO 2
<211> LENGTH: 7
<212> TYPE: DNA
<213> ORGANISM: Human

<400> SEQUENCE: 2 ccaaacc       7

<210> SEQ ID NO 3
<211> LENGTH: 6
<212> TYPE: DNA
<213> ORGANISM: Human

<400> SEQUENCE: 3 ggtttg       6

<210> SEQ ID NO 4
<211> LENGTH: 15
<212> TYPE: DNA
<213> ORGANISM: Human

<400> SEQUENCE: 4
gtctaaagat ggtga       15